United States Patent [19]

Janiak

[11] 3,951,641

[45] Apr. 20, 1976

[54] USE OF N-(4-ISOPROPOXY-3-CHLOROPHENYL)-N'-METHYL-N'-METHOXYUREA FOR CONTROL OF WEEDS IN MAIZE CULTURES

[75] Inventor: Stefan Janiak, Basel, Switzerland

[73] Assignee: Ciba-Geigy AG, Basel, Switzerland

[22] Filed: Sept. 26, 1974

[21] Appl. No.: 509,574

Related U.S. Application Data

[62] Division of Ser. No. 259,330, June 2, 1972, abandoned, which is a division of Ser. No. 59,703, July 30, 1970, abandoned.

[30] Foreign Application Priority Data

Aug. 5, 1969   Switzerland.................. 11887/69

[52] U.S. Cl.............................. 71/120; 260/453 R; 260/553 A; 71/76
[51] Int. Cl.² ......................................... A01N 9/20
[58] Field of Search................ 71/120; 260/453 R

[56] References Cited
UNITED STATES PATENTS

| | | | |
|---|---|---|---|
| 2,655,445 | 10/1953 | Todd | 71/120 |
| 2,655,447 | 10/1953 | Todd | 71/120 |
| 2,723,192 | 11/1955 | Todd | 71/120 |
| 3,112,342 | 11/1963 | Lockenbaugh | 71/120 |
| 3,288,851 | 11/1966 | Martin et al. | 71/120 |

*Primary Examiner*—Glennon H. Hollrah
*Attorney, Agent, or Firm*—Frederick H. Rabin

[57] ABSTRACT

New phenylureas of the formula

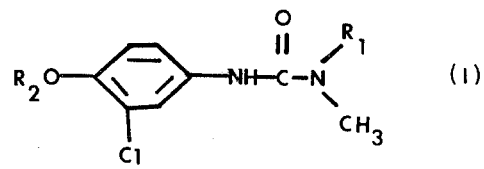

(1)

in which $R_1$ represents a methyl or a methoxy group and $R_2$ represents a n-propyl or i-propyl group, a process for their manufacture and their use as pesticides.

1 Claim, No Drawings

USE OF N-(4-ISOPROPOXY-3-CHLOROPHENYL)-N'-METHYL-N'-METHOXYUREA FOR CONTROL OF WEEDS IN MAIZE CULTURES

This is a division of application Ser. No. 259,330, filed on June 2, 1972 which is a division of application Ser. No. 59,703, filed on July 30, 1970, both now abandoned.

This invention relates to 4-propoxy-3-chlorophenylureas, a process for their preparation and to their use as pesticides.

The present invention provides compounds of the formula

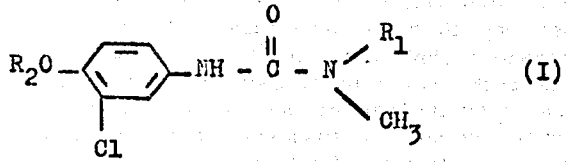

in which $R_1$ represents a methyl or a methoxy group and $R_2$ represents a n-propyl or i-propyl group.

The phenylureas of the formula (I) may be prepared according to methods which are in themselves known, for example according to the following reaction scheme:

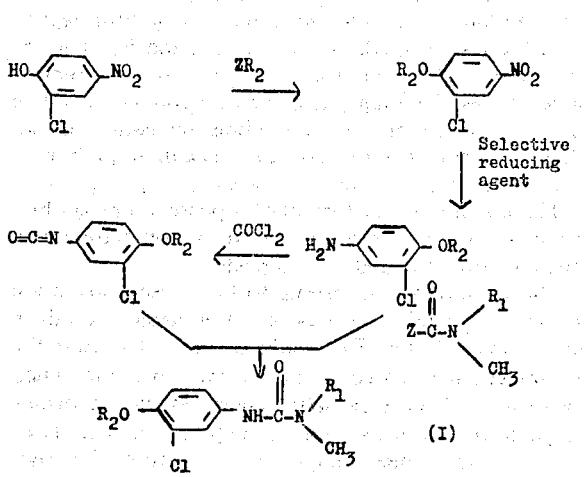

The following process is however preferably used for the preparation of the compounds of the present invention:

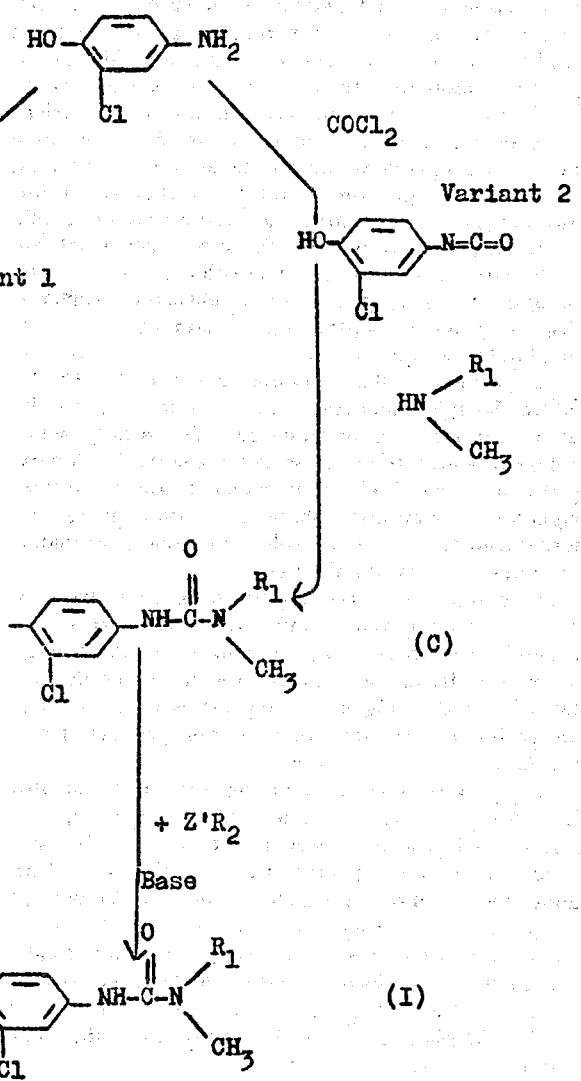

It will be clear that after the preparation of the compound (C), the latter can be O-alkylated in the presence of a base. This process, starting from a hydroxyphenylurea (C), enables the products of the invention to be obtained with the most diverse alkylating agents.

In the above reaction schemes, $R_1$ and $R_2$ have the meanings specified above. Z and Z' represent removable groups, for example, chlorine, bromine or iodine atoms. Triethylamine and pyridine, potassium- or sodium bicarbonate or potassium- or sodium carbonate can, for example, be used as bases.

The compounds of formula (I) possess a broad biocidal action and can be employed for combatting very diverse vegetable and animal pests.

The compounds according to the present invention possess, especially, a selective action against weeds in crop plant cultures. This action can be achieved in the pre-emergence process and in the post-emergence process and is especially observed in important large-scale cultures, for example, cereals, rice, maize, sugar beet, soya, peas, cotton, lucerne, potatoes and others. The amounts of the compounds used can vary within wide limits, for example between 0.1 and 10 kg of the active substance per hectare, but preferably from 0.5 to 5 kg per hectare are employed. A total herbicidal and also defoliating action is observed if higher amounts are used, and this action is of advantage in all cases where the culture soil is to be prepared for a new planting whilst remnants of a previous culture are still present.

The compounds of the present invention may be used by themselves or in admixture with a suitable carrier.

Accordingly, the present invention also provides a pesticidal preparation comprising, as active ingredient, a compound of general formula I, together with a suitable carrier. Suitable carriers and additives can be solid or liquid and correspond to the substances which are customary in formulation technology, for example, natural or regenerated mineral substances, solvents, dispersing agents, wetting agents, adhesives, thickeners, binders and fertilisers.

Furthermore, other biocidal compounds can be added. Such biocidal compounds can, for example, be ureas, saturated or unsaturated halogen-fatty acids, halogenobenzonitriles, halogenobenzoic acids, phenoxyalkylcarboxylic acids, carbamates, triazines, nitroalkylphenols, organic phosphoric acid compounds, quaternary ammonium salts, sulphamic acids, arsenates, arsenites, borates or chlorates.

The compounds according to the present invention can also be employed for influencing plant growth, for example, for accelerating ripening in plants through premature drying-out, and also for increasing the setting of fruit, delaying blossoming, extending the storage life of harvest products or rendering products frost-resistant.

The use of the growth-inhibiting compounds can also lead to an increase in yield not only through suppressing weeds but also through counteracting influences which stimulate the growth of the culture plants in an undesired direction, such as for example high temperature or copious fertilisation. Alternatively, the herbicides can be of interest from a long-term point of view when destroying obstinate weeds, if the selectivity of the agent does not suffice to exclude a reduction in yield of the plants grown at the time of use of the compound.

The preparations according to the invention can be employed in the form of solutions, emulsions, suspensions, granules or dusting agents. The particular form depends on the end use and must ensure fine divisibility of the active ingredient. In particular, in the case of the total destruction of plants, in the case of premature drying-out and in the case of defoliation, the action can be intensified by the use of carriers which are in themselves phytotoxic, for example, high-boiling mineral oil fractions or chlorinated hydrocarbons; on the other hand, the selectivity of inhibition of growth in general manifests itself distinctly when using carriers which are inert towards plants, for example in selective combatting of weeds.

To manufacture solutions it is possible to use solvents, especially alcohols, for example, ethyl alcohol or isopropyl alcohol, ketones, such as acetone or cyclohexanone, aliphatic hydrocarbons, such as kerosene, and cyclic hydrocarbons, such as benzene, toluene, xylene, tetrahydronaphthalene and alkylated naphthalenes, chlorinated hydrocarbons, such as tetrachlorethane and ethylene chloride, and also mineral and vegetable oils or mixtures of the above-mentioned substances.

The aqueous preparations are preferably dispersions. The active substances, as such or in one of the above-mentioned solvents, are homogenised in water, preferably by means of wetting agents or dispersing agents. Quaternary ammonium compounds may be mentioned as examples of cationic dispersing agents, soaps, aliphatic long-chain sulphuric acid monoesters, aliphatic-aromatic sulphonic acids and long-chain alkoxyacetic acids may be mentioned as examples of anionic dispersing agents and polyglycol ethers of fatty alcohols or ethylene oxide condensation products with p-tert.alkylphenols may be mentioned as non-ionic dispersing agents. On the other hand, it is also possible to manufacture concentrates consisting of active substance, dispersing agent and possibly solvents, these being suitable for dilution with water before use.

Dusting agents can be manufactured by mixing or conjoint grinding of the active substance with a solid carrier. Possible carriers are for example talc, diatomaceous earth, kaoline, bentonite, calcium carbonate, boric acid and tri-calcium phosphate, wood flour, cork powder, charcoal and other materials of vegetable origin. On the other hand, the substances can also be absorbed on the carriers, for example, using a volatile solvent. Pulverulent preparations and pastes can be rendered capable of suspension in water, and used as spraying agents, by adding wetting agents and protective colloids.

In many cases the use of granules for the uniform release of active substances over a longer period of time is of advantage. These granules can be manufactured by dissolving the active substance in an organic solvent, absorbing this solution by granular material, for example attapulgite or $SiO_2$, and removing the solvent. They can also be manufactured by mixing the active substances of formula I with polymerisable compounds, after which polymerisation is carried out which leaves the active substances unaffected, with the granulation being carried out whilst the polymerisation is still proceeding.

It is also possible to apply such agents by distribution over large areas (spraying, dusting and the like) with the aid of aircraft.

The various forms of such preparations can be more closely suited to the end uses in the customary manner by addition of substances which improve the distribution, the adhesion, the rain resistance and, where relevant, the penetrating power, such as, for example, fatty acids, resins, wetting agents, glue, casein or alginates.

In the manufacture of herbicidally active agents the following components can furthermore, for example, be employed for combination purposes.

A. SUBSTITUTED UREAS

N-Phenyl-N'N'-dimethyl-urea
N-Phenyl-N-hydroxy-N',N'-dimethyl-urea
N-(4-Chlorophenyl)-N',N'-dimethyl-urea
N-(3,4-Dichlorophenyl)-N',N'-dimethyl-urea
N-(3,4-Dichlorophenyl)-N-benzoyl-N',N'-dimethyl-urea
N-(4-Chlorophenyl)-N'-methoxy-N'-methyl-urea
N-(4-Chlorophenyl)-N'-isobutinyl-N'-methyl-urea
N-(3,4-Dichlorophenyl)-N'-methoxy-N'-methyl-urea
N-(4-Bromophenyl)-N'-methoxy-N'-methyl-urea
N-(4-Chlorophenyl)-N'-methyl-N'-butyl-urea
N-(4-Chlorophenyl)-N'-methyl-N'-isobutyl-urea
N-(2-Chlorophenoxyphenyl)-N',N'-dimethyl-urea
N-(4-Chlorophenoxyphenyl)-N',N'-dimethyl-urea
N-(4-Chlorophenyl)-N'-methyl-N'-(1-butin-2-yl)-urea
N-Benzthiazol-2-yl-N',N'-dimethyl-urea
N-Benzthiazol-2-yl-N'-methyl-urea
N-(3-Trifluoromethyl-4-methoxyphenyl)-N',N'-dimethyl-urea
N-(3-Trifluoromethyl-4-isopropoxyphenyl)-N',N'-dimethyl-urea
N-(3-Trifluoromethylphenyl)-N',N'-dimethyl-urea
N-(4-Trifluoromethylphenyl)-N',N'-dimethyl-urea
N-(4-Chlorophenyl)-N'-(3'-trifluoromethyl-4'-chlorophenyl)-urea N-(3,4-Dichlorophenyl)-N'-methyl-N'-butyl-urea
N-(3-Chloro-4-trifluoromethylphenyl)-N',N'-dimethyl-urea
N-(3-Chlor-ethylphenyl)-N',N'-dimethyl-urea
N-(3-Chloro-4-methylphenyl)-N',N'-dimethyl-urea
N-(3-Chlor-ethoxyphenyl)-N'-methyl-N'-methoxy-urea
N-(3-Chloro-4-methoxyphenyl)-N',N'-dimethyl urea
N-(Hexahydro-4,7-methanoindan-5-yl)-N',N'-dimethyl-urea
N-(2-Methylcyclohexyl)-N'-phenyl-urea
N-(4,6-Dichloro-2-pyridyl)-N'-dimethyl-urea
N'-Cyclooctyl-N,N-dimethyl-urea
Dichloro-urea
N'-4-(4-Methoxyphenoxy)phenyl-N,N-dimethyl-urea
N'-(3-Methylphenyl)-N,N-dimethyl-thiourea
1,1-Dimethyl-3,-[3-(N-tert.butylcarbamoyloxy)-phenyl]-urea
O,N,N-Trimethyl-N'-4-chlorophenyl-isourea
N-3,4-Dichlorophenyl-N',N'-dimethyl-α-chloroformamidine
N,N-Dimethyl-N'-phenyl-urea-trichloracetate
N,N-Dimethyl-N'-4-chlorophenyl-urea-trichloracetate

B. SUBSTITUTED TRIAZINES

2-Chloro-4,6-bis(ethylamino)-s-triazine
2-Chlor-4-ethylamino-6-isopropylamino-s-triazine
2-Chloro-4,6-bis(methoxypropylamino)-s-triazine
2-Methoxy-4,6-bis(isopropylamino)-s-triazine
2-Diethylamino-4-isopropylacetamido-6-methoxy-s-triazine
2-Isopropylamino-4-methoxyethylamino-6-methylmercapto-s-triazine
2-Methylmercapto-4,6-bis(isopropylamino)-s-triazine
2-Methylmercapto-4,6-bis(ethylamino)-s-triazine
2-Methylmercapto-4-ethylamino-6-tert.butylamino-s-triazine
2-Methylmercapto-4-ethylamino-6-isopropylamino-s-triazine 2-Methylmercapto-4-methylamino-6-isopropylamino-s-triazine
2-Methoxy-4,6-bis(ethylamino)-s-triazine
2-Methoxy-4-ethylamino-6-isopropylamino-s-triazine
2-Chloro-4,6-bis(isopropylamino)-s-triazine
2-Azido-4-methylmercapto-6-isopropylamino-s-triazine
2-Azido-4-methylmercapto-6-sec.butylamino-s-triazine
2-Chlor-4-isopropylamino-6-(γ-methoxypropylamino)-s-triazine
2-(6-Ethylamino-4-chloro-s-triazin-2-yl-amino)-2-methyl-propionitrile
2-Chloro-4-diethylamino-6-isopropylamino-s-triazine
2-Methoxy-4,6-bis-(3-methoxypropylamino)-s-triazine
2-Methylmercapto-4-isopropylamino-6-(3-methoxypropylamino)-s-triazine
2-Chloro-4-diethylamino-6-ethylamino-s-triazine
2,4-Bis(3-methoxypropylamino-6-methylthio-1,3,5-triazine
2-Methylthio-4-isopropylamino-6-(γ-methoxypropylamino)1,3,5-triazine
2-Chlor-4-ethylamino-6-tert.butylamino-s-triazine
2-(4-Chlor-6-ethylamino-1,3,5-triazin-2-yl-amino)-2-methyl-propionitrile.

C. PHENOLS

| | |
|---|---|
| Dinitro-sec-butylphenol or salts thereof | |
| Pentachlorophenol or salts thereof | |
| 3,5-Dinitro-o-cresol | |
| 2,6-Dibromo-4-cyanphenol | |
| 2,6-Dichloro-4-cyanphenol | salts + esters |
| Dinitro-tert-butylphenol | salts + esters |
| Dinitro-sec-amyl-phenol | salts + esters |
| 2-Ethoxymethyl-4,6-dinitrophenol | salts + esters |
| 2-tert-Butyl-4,6-dinitro-5-methylphenol | salts + esters |

D. CARBOXYLIC ACIDS, SALTS AND ESTERS 2,4,6-Trichlorophenylacetic acid
2,3,6-Trichlorobenzoic acid and salts
2,3,5,6-Tetrachlorobenzoic acid and salts
2,3,5,6-Tetrachloroterephthalic acid
2-Methoxy-3,5,6-trichlorobenzoic acid and salts
Cyclopropanecarboxylic acid 2,4-dinitro-6-sec.butylphenyl ester
Cyclopentanecarboxylic acid 2,4-dinitro-6-sec.butylphenyl ester
2-Methoxy-3,6-dichlorobenzoic acid and salts
2-Amino-2,5-dichlorobenzoic acid and salts
3-Nitro-2,5-dichlorobenzoic acid and salts
2-Methyl-3,6-dichlorobenzoic acid and salts
2,4-Dichlorophenoxyacetic acid, salts and esters
2,4,5-Trichlorophenoxyacetic acid, salts and esters
(2-Methyl-4-chlorophenoxy)acetic acid, salts and esters
2-(2,4,5-Trichlorophenoxy)propionic acid, salts and esters 2-(2,4,5-Trichlorophenoxy)ethyl-2,2-dichloropropionic acid, salts and esters
4-(2,4-Dichlorophenoxy)butyric acid, salts and esters
4-(2-Methyl-4-chlorophenoxy)butyric acid    salts + esters
Methyl-2-chloro-3-(4'-chlorophenyl)-propionate
2-Chloro-9-hydroxy-fluorene-9-carboxylic acid
Endo-oxo-hexahydrophthalic acid
Tetrachlorophthalic acid dimethyl ester
4-Chloro-2-oxobenzothiazolin-3-yl-acetic acid
2,2,3-Trichloropropionic acid    salts + esters
2,2-Dichloropropionic acid    salts + esters
(±)2-(2,4-Dichlorophenoxy)-propionic acid    salts + esters
7-Oxabicyclo(2,2,1)heptano-2,3-dicarboxylic acid
4-Chlorophenoxyacetic acid    salts + esters
Gibberellic acid
Indolylacetic acid
Indolylbutyric acid
(±)2-(4-Chloro-2-methylphenoxy)propionic acid    salts + esters
N,N-Diallylchloracetamide
Naphthylacetic acid
N-1-Naphthylphthalimide-acid    salts + esters
4-Amino-3,5,6-trichloro-picolinic acid    salts + esters
Trichloracetic acid
4-(2,4,5-Trichlorophenoxy)butyric acid    salts + esters
2,3,5-Triiodobenzoic acid    salts + esters
Benzimidoxyacetic acid    salts + esters
Ethylene glycol-bis-trichloracetate
Chloracetic acid diethylamide
2,6-Dichlorothiobenzamide
2,6-Dichlorobenzonitrile
N,N-Dimethyl-α,α-diphenylacetamide
Diphenylacetonitrile
N-Hydroxymethyl-2,6-dichlorothiobenzamide

E. CARBAMIC ACID DERIVATIVES

Carbanilic acid isopropyl ester
3,4-Dichloro-carbanilic acid methyl ester
m-Chloro-carbanilic acid isopropyl ester
m-Chloro-carbanilic acid 4-chloro-2-butinyl ester
m-Trifluoromethyl-carbanilic acid isopropyl ester
2,6-Di-tert.butyl-4-tolyl-N-methylcarbamate
3-(Methoxycarbonylamino)phenyl-N-3-tolylcarbamate
4-Chloro-2-butinyl-N-(3-chlorophenyl)-carbamate
Methyl 2-isopropyl-4-(methylcarbamoyloxy)carbanilate, and also Diallate, N,N-dipropyl-S-ethylthiocarbamate, molinates and dithiocarbamates of formula

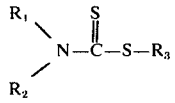

wherein $R_1$, $R_2$ and $R_3$ denote a lower alkyl or alkenyl radical, or wherein $R_1$ and $R_2$ together with the nitrogen atom to which they are bonded represent a 5-membered, 6-membered or 7-membered, optionally alkylated ring with a total of 6 or 7 C atoms, it being necessary for the exo-alkyl groups to be bonded to the carbon atoms adjacent to the nitrogen atom, and $R_3$ represents the ethyl, propyl, n-butyl or isobutyl radical, and amongst these especially N-Butyl-N-ethyl-S-propyl-dithiocarbamate
   N,N-Diisobutyl-S-propyl-dithiocarbamate
   N,N,S-Tripropyldithiocarbamate
   N-Isobutyl-N-allyl-S-propyldithiocarbamate
   N-Isobutyl-N-methallyl-S-ethyldithiocarbamate
   N-Isobutyl-N-methallyl-S-propyldithiocarbamate
   N,N-Dimethallyl-S-propyldithiocarbamate
   N-Butyl-N-ethyl-S-propyl-thiocarbamate and
   N,N,S-Tripropylthiocarbamate, and also
   N-(4-Aminobenzsulphonyl)methylcarbamate
   1-Methylprop-2-yl-N-(3-chlorophenyl)carbamate
   Isopropyl-N-(3-chlorophenyl)-carbamate
   S-2,3-Dichlorallyl-N,N-diisopropylthiocarbamate
   S-Ethyl-N,N-dipropylthiolcarbamate
   N-Methyldithiocarbamic acid
   S-Propyl-N-butyl-N-ethylthiolcarbamate
   3-(m-Tolylcarbamoyloxy)-phenylcarbamate
   Isopropyl-N-phenylcarbamate
   2-Chlorallyl-N,N-diethyldithiocarbamate
   Methyl-N-(3,4-dichlorophenyl)carbamate
   S-2,3,3-Trichlorallyl-N,N-diisopropylthiolcarbamate
   S-Propyl-N,N-dipropylthiolcarbamate
   S-Ethyl-N-ethylthiocyclohexanecarbamate
   3,4-Dichlorobenzylmethylcarbamate
   S-Ethyl-N-hexahydrol-1H-azepinethiolcarbamate
   2,6-Di-t-butyl-4-methylphenyl-N-methylcarbamate
   Methyl-N-(4-nitrobenzsulphonyl)carbamate
   N,N-hexamethylen-S-isopropylthiocarbamate
   S-Ethyl-N,N-diisobutylthiolcarbamate
   2-Chlorobutinyl-N-(3-chlorophenyl)carbamate
   S-Ethyl-N,N-diisobutylthiolcarbamate
   Methyl-N'-(N'-methoxycarbamoyl-sulphanilyl)carbamate

F. ANILIDES 3,4-Dichloropropionanilide
   3-Chloro-4-bromopropionanilide
   3-Bromo-4-chloropropionanilide
   Cyclopropanecarboxylic acid 3,4-dichloranilide
   Cyclopropanecarboxylic acid 3-chloro-4-bromanilide
   Cyclopropanecarboxylic acid 3-bromo-4-chloranilide
   N-(3,4-Dichlorophenyl)-2-methylpentanamide
   N-1-naphthyl-phthalamic acid
   N-(3-Tolyl)-phthalamic acid
   2-Methacryl-3',4'-dichloranilide
   N-(4-Chlorophenyl)-2,2-dimethylvaleramide
   N-(3-Chloro-4-methylphenyl)-2-methylpentanamide
   α-Chloro-N-isopropylacetanilide
   2-(α-Naphthoxy)-N,N-diethylpropionamide
   2-Chloro-N-(2-methyl-6-tert.butylphenyl)acetamide
   2-Chloro-N-2,6-diethylphenyl-N-methoxymethylacetamide
   6-Methyl-N-methoxymethyl-2-t-butyl-α-bromacetanilide
   2-[(4-Chlor-o-tolyl)oxy]-N-methoxyacetamide
   2-Chlor-N-isopropyl-acetanilide

G. ORGANIC PHOSPHORUS COMPOUNDS tris-(2,4-Dichlorophenoxyethyl)phosphite
   O-(2,4-Dichlorophenyl)-O'-methyl-N-isopropylamidothio-phosphate
   N-[2-(O,O-Di-isopropyldithiophosphoryl)ethyl]benzenesulphonamide
   S,S,S-Tributyl-thiophosphate

H. VARIOUS COMPOUNDS 4,5-Dichloro-2-trifluoromethylbenzimidazole
   2-Chlorethyl-trimethyl-ammonium chloride
   Maleic acid hydrazide
   Methylarsinic acid di-Na salt
   4,5,7-Trichlorobenzthiodiazole-2,1,3
   3-Amino-1,2,4-triazole
   Trichlorobenzyl chloride
   2-Phenyl-3,1-benzoxazinone
   N-Butyl-N-ethyl-2,6-dinitro-4-trifluoromethylaniline N,N-Di-(n-propyl)-2,6-dinitro-4-trifluoromethylaniline
4-Trifluoromethyl-2,4'-dinitro-diphenyl-ether
2,4,6-Trichloro-4'-nitrodiphenyl-ether
4-Trifluoromethyl-2,4'-dinitro-3'-methyl-diphenyl-ether
2,4-Dichloro-4'-nitro-diphenyl-ether
5-Chloro-6-methyl-3-tert.butyl-uracil
Ammonium sulphamate
5-Bromo-6-methyl-3-(1-methyl-N-propyl)-uracil
1,2,4,5,6,7,10,10-Octachloro-4,7,8,9-tetrahydro-4,7-methyleneindane-m-isopropyl-xanthate
5-Brom-3-isopropyl-6-methyluracil
3-Cyclohexyl-6-methyluracil
3-Cyclohexyl-6-sec-butyluracil
3-Cyclohexyl-5-bromuracil
3-Cyclohexyl-5-chloruracil
3-Cyclohexyl-5,6-trimethylene-uracil
3-Isopropyl-5-chloruracil
3-Isopropyl-5-bromuracil
2-Chlor-N-ethyl-4-thiocyanatoaniline
2,3,6-Trichlorobenzyloxypropanol
Hexachloro-2-propanone
Sodium 2-(2,4,5-trichlorophenoxy)-ethyl-sulphate
Potassium cyanate
3,5-Dibromo-4-hydroxybenzaldoxime-2',4'-dinitrophenyl-ether
3,5-Diiodo-4-hydroxybenzaldoxime-2',4'-dinitrophenyl-ether
Acrolein
Arsenates
Allyl alcohol
2,4-Dinitrophenyl,2,4-dinitro-6-sec.butylphenylcarbonate
5-Chlor-2-isopropylbenzimidazole
5-Iodo-2-trifluoromethylbenzimidazole
3-Cyclohexyl-6,7-dihydro-1H-cyclopentapyrimidine 2,4-(3H,5H)dione
1:1-Ethylene-2:2-bipyridylium bromide
1,1-Dimethyl-4,4'-bipyridylium-dimethyl-sulphate
Di(methoxycarbonyl)disulphide
2-Methyl-4-(3'-trifluoromethylphenyl)-tetrahydro-1,2,4-oxadiazine-3,5-dione
1-Phenyl-4,5-dimethoxy-6-pyridazone
6-Chloro-2-difluoromethyl 3H-imidazo(4,5-b)-pyridine
2-tert.Butyl-6-chlorimidazo-4,5-pyridine
5-Amino-4-bromo-2-phenylpyridazin-3-one Hexafluoroacetone hydrate
3,5-Dinitro-4-dipropylamino-benzenesulphonamide
Cacodyl
4-(Methylsulphonyl)-2,6-dinitro-N,N-dipropylaniline
4-Methyl-2,6-dinitro-N,N-dipropylaniline
5-Amino-4-chloro-2-phenyl-3-pyridazone
2,3,5-Trichloro-4-pyridinol
3,4,5,6-Tetrahydro-3,5-dimethyl-1,3,5-thiadiazine-2-thione
Sodium 2-(2,4-dichlorophenoxy)ethyl-sulphate
2,3-Dichloro-1,4-naphthoquinone
Di(ethoxythiocarbonyl)disulphide
3,5-Dichloro-2,6-difluoro-4-hydroxy-pyridine The content of active substance in the agents described above lies between 0.1 and 95 %. Here is should be mentioned that concentrations of up to 99.5 % or even pure active substance are employed in the case of application from aircraft or by means of other suitable application instruments.

EXAMPLE 1

Manufacture of the compound No. 1.1 of formula

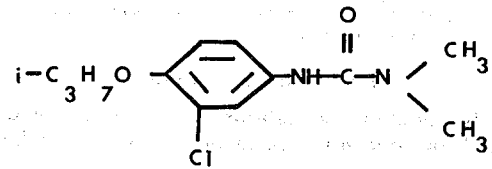

31.8 g of p-isopropoxy-m-chloro-phenylisocyanate, 15 % strength in ethyl acetate, were added dropwise, with vigorous stirring, to a mixture of 19 ml of dimethylamine, 200 ml of petroleum ether (50–70), 20 ml of ethyl acetate and 0.1 g of triethylenediamine [1,4-diazabicyclo(2,2,2) octane]. The mixture was stirred for 3 hours and the precipitated product was subsequently filtered off. The residue was recrystallised from benzene-petrol.
Melting point 108° – 109°C; yield 36.5 g.
The following compounds were also manufactured analogously:

1.2 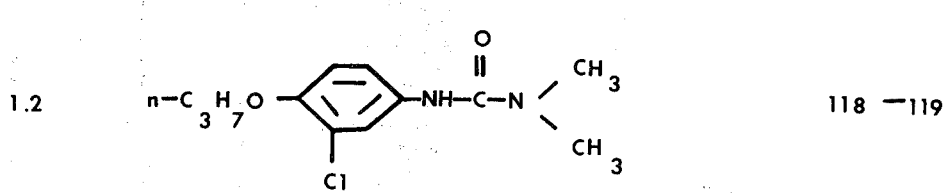 118 –119

1.3 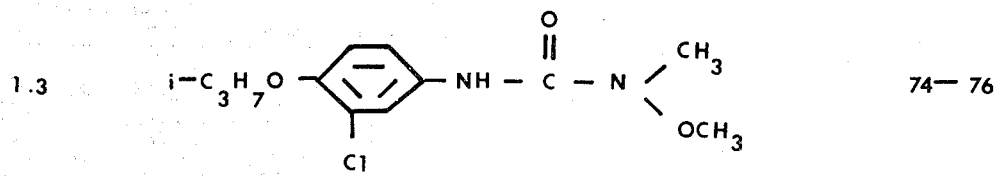 74– 76

1.4 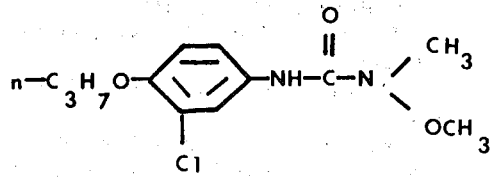 79—80

EXAMPLE 2
Dusting Agents

Equal parts of an active substance of formula I and of precipitated silica were finely ground. The dusting agents, preferably containing 1–6 % of active substance, could be manufactured therefrom by mixing with kaolin or talc.

Spraying Powders

To manufacture a spraying powder, the following components were for example mixed and finely ground:

| | |
|---|---|
| 50 | parts of active substance according to the present invention |
| 20 | parts of highly adsorbent silica |
| 25 | parts of Bolus alba (kaolin) |
| 1.5 | parts of sodium 1-benzyl-2-stearyl-benzimidazole-6,3'-disulphonate and |
| 3.5 | parts of a reaction product of p-tert. octylphenol and ethylene oxide. |

Emulsion Concentrate

Easily soluble active substances were formulated as an emulsion concentrate in accordance with the following directions:

| | |
|---|---|
| 20 | parts of active substance |
| 70 | parts of xylene and |
| 10 | parts of a mixture of a reaction product of an alkylphenol with ethylene oxide and calcium dodecylbenzenesulphonate | are mixed. On dilution with water to the desired concentration, a sprayable emulsion was produced.

Granules 7.5 g of an active substance of formula I were dissolved in 100 ml of acetone and the acetone solution thus obtained was added to 92 g of granular attapulgite. The whole was well mixed and the solvent was driven off in a rotary evaporator. Granules containing 7.5 % of active substance were obtained.

EXAMPLE 3

The following varieties of plants were sown in a greenhouse: *Triticum vulgare, Hordeum, Zea mays, Oryza, Gossypium, Soja, Alopecurus, Poa, Amaranthus, Panicum, Chrysanthemum, Linum, Sorghum, Calendula, Stellaria, Digitaria, Galium, Beta, Brassica* and *Ipomoea*.

The post-emergent treatment of the varieties of plants mentioned was carried out with 1 % strength aqueous solution of compounds 1.1, 1.2, 1.3 and 1.4 approximately 10–12 days after sowing, in the 2–3 leaf stage, using an amount of 1 kg of active substance per hectare.

The pre-emergent treatment was carried out using the same amount, but already 24 hours after sowing.

The evaluation in both processes took place about 20 days after the treatment and led to the figures reproduced in the Table below.

| Variety of Plant | Compound 1.1 1 kg/hectare pre | Compound 1.2 1 kg/hectare post | Compound 1.2 1 kg/hectare pre | Compound 1.3 1 kg/hectare post | Compound 1.3 1 kg/hectare pre | Compound 1.4 1 kg/hectare post | Compound 1.4 1 kg/hectare pre |
|---|---|---|---|---|---|---|---|
| Triticum | 1 | — | 2 | 1 | 1 | 2 | |
| Hordeum | 2 | — | 3 | — | 3 | — | |
| Zea Mais | 2 | 2 | 3 | — | — | 1 | |
| Oryza | — | — | 2 | — | — | — | |
| Gossypium | — | — | 1 | — | 1 | — | |
| Soja | — | — | 3 | — | — | — | |
| Digitaria | 6 | 9 | — | 9 | 9 | — | |
| Sorghum | — | 9 | — | — | — | 8 | |
| Panicum | — | 9 | — | 8 | 7 | 8 | |
| Poa | 7 | 9 | 9 | 9 | 9 | 9 | |
| Alopecurus | 7 | 6 | 8 | 9 | 9 | — | |
| Beta | 7 | 9 | — | 9 | 9 | 9 | |
| Galium | — | 7 | — | 9 | — | — | |
| Calendula | 9 | 9 | 9 | 9 | 9 | 9 | |
| Chrysanthemum | 8 | 9 | 9 | 9 | 9 | 9 | |
| Linum | 8 | — | — | 9 | 9 | 9 | |
| Brassica | 9 | 8 | 9 | 9 | 9 | 9 | |
| Ipomoea | 9 | 9 | 9 | 9 | 9 | 9 | |
| Stellaria | 9 | 9 | 9 | 9 | 9 | 9 | |
| Amaranthus | 9 | 9 | 9 | 9 | 9 | 9 | |

Assessment Scheme

| Rating | Action, % | Action | Damage to Plants |
|---|---|---|---|
| 1 | 0 | none | none |
| 2 | up to −12.5 | very slight | light |
| 3 | −25 | slight | light-medium |
| 4 | −37.5 | moderate | medium |
| 5 | −50 | average | medium-strong |
| 6 | −62.5 | not yet sufficient | strong |
| 7 | −75 | just sufficient | strong, partly leading to death |
| 8 | −87.5 | good | strong, leading to death |
| 9 | −100 | very good | total (plants dead) |

I claim:
1. A method for combating weeds in maize cultures which comprises applying thereto a herbicidally effective amount of N-(4-isopropoxy-3-chlorophenyl)-N'-methyl-N'-methoxyurea.

* * * * *